United States Patent
Liao et al.

(10) Patent No.: US 11,293,918 B2
(45) Date of Patent: Apr. 5, 2022

(54) METHOD AND KIT FOR SIMULTANEOUS DETECTION OF MULTI TARGET MOLECULES USING MAGNETIC BEAD-APTAMER CONJUGATE

(71) Applicant: Shiqi Liao, Lanzhou (CN)

(72) Inventors: Shiqi Liao, Lanzhou (CN); Jiayu Zeng, Lanzhou (CN); Zhengyu Liao, Lanzhou (CN); Yi Li, Lanzhou (CN); Hongxia Yuan, Lanzhou (CN); Zhengli Wei, Lanzhou (CN)

( * ) Notice: Subject to any disclaimer, the term of this patent is extended or adjusted under 35 U.S.C. 154(b) by 0 days.

(21) Appl. No.: 16/658,092

(22) Filed: Oct. 20, 2019

(65) Prior Publication Data

US 2020/0116711 A1    Apr. 16, 2020

Related U.S. Application Data

(63) Continuation of application No. PCT/CN2018/090472, filed on Jun. 8, 2018.

(51) Int. Cl.

| | | |
|---|---|---|
| *C07H 21/04* | (2006.01) | |
| *G01N 33/543* | (2006.01) | |
| *G16B 40/10* | (2019.01) | |
| *C12N 15/115* | (2010.01) | |
| *G01N 33/52* | (2006.01) | |
| *G01N 33/68* | (2006.01) | |
| *C12N 15/10* | (2006.01) | |

(52) U.S. Cl.
CPC ..... *G01N 33/54306* (2013.01); *C12N 15/115* (2013.01); *G01N 33/52* (2013.01); *G01N 33/54333* (2013.01); *G01N 33/6848* (2013.01); *G16B 40/10* (2019.02); *C12N 15/1048* (2013.01); *C12N 2310/16* (2013.01); *C12Q 2541/101* (2013.01)

(58) Field of Classification Search
CPC ......................... C12N 2310/16; C12N 2320/13
See application file for complete search history.

(56) References Cited

U.S. PATENT DOCUMENTS

| | | | |
|---|---|---|---|
| 10,288,606 B2 | 5/2019 | Sugimoto et al. | |
| 2011/0124015 A1 | 5/2011 | Tan et al. | |
| 2017/0219491 A1 | 8/2017 | Li et al. | |

FOREIGN PATENT DOCUMENTS

| | | | | |
|---|---|---|---|---|
| CN | 104450713 A | * | 3/2015 | ......... C12N 2310/16 |
| CN | 105018590 A | | 11/2015 | |
| CN | 106353499 A | | 1/2017 | |

OTHER PUBLICATIONS

Aquino-Jarquin et al. (Int. J. Mol. Sci., 2011, 12, 9155-9171).*
Bruno et al. (Microchemical Journal, 2016, 124, 90-95).*
Zhang et al. (Biosensors and Bioelectronics, 2016, 86, 736-740).*
Freitas et al. (Clinical Biochemistry, 41, 2008, 570-575).*
Atuma et al. (Bull. Environ. Contam. Toxicol., 1999, 62, 8-15).*

* cited by examiner

*Primary Examiner* — Amy H Bowman

(57) ABSTRACT

This application relates to molecular biology, and more specifically to a method which uses the molecular recognition between a target molecule ligand and an aptamer, magnetic separation and MS qualitative and quantitative analysis to enable the association between the detection of multi molecules and information of multiple functional groups, and effectively determine the correlation between molecules and functional groups of the body or tissue. This application can easily purify the target molecules by magnetic separation and can effectively obtain the target molecule group based on the high specificity and affinity of the aptamer. In addition, based on the MS detection, this application can effectively perform the qualification and quantification of the multi molecules, achieving the secondary molecular detection and improving the detection accuracy. The simultaneous qualification and quantification of multi molecules can not only accurately reflect the relationship among molecules, but also reveal the interrelationship among body functions, playing a significant role in the proteomics and genomics research and clinical molecular detection.

7 Claims, 3 Drawing Sheets

METHOD AND KIT FOR SIMULTANEOUS DETECTION OF MULTI TARGET MOLECULES USING MAGNETIC BEAD-APTAMER CONJUGATE

CROSS-REFERENCE TO RELATED APPLICATIONS

This application is a continuation of International Patent Application No. PCT/CN2018/090472 with a filing date of Jun. 8, 2018, designating the United States. The content of the aforementioned applications, including any intervening amendments thereto, are incorporated herein by reference.

TECHNICAL FIELD

This application relates to a method and a kit for simultaneous detection of multi target molecules, and more particularly to a method for qualitative and quantitative detection of the target molecules by capturing markers in samples with magnetic bead-aptamer complexes by means of Laser Desorption/Ionization-TOF-MS and analyzing data on a data platform to obtain the results. In general, the present application is directed to the detection of target molecules and comprehensive analysis of a system.

BACKGROUND OF THE INVENTION

Early protein detection is performed based on a low dissociation constant of a conjugate of an antibody and a specific protein to be detected and a certain specificity of the antibody, where the protein is generally screened by antibody capture ELISA. The antibody capture ELISA specifically comprises the following steps: coating an antigen with a solid phase support material; using an antibody to bind the antigen; removing the unbound antibody by washing; and detect the bound antibody with a marker capable of specifically recognizing the bound antibody. The antibody is often detected indirectly in many antibody capture ELISAs, for example, the detection molecule may be a rabbit anti-mouse antibody carrying a detection marker in the use of a murine antibody as the detection antibody. Conventional detection markers comprise radioisotopes, dyes, and enzymes that act on substrates to produce detectable molecules such as chromogens.

The antigen capture ELISA is used to determine whether there is an antigen in the sample. In this method, an antibody is first bound to a support material, and then the antigen is added to react with the antibody to form a complex which is finally used for detection; or the antibody first reacts with the antigen to form the complex, and then the complex is bound to a solid phase support material for detection.

ELISA is a currently well-known immunoassay, of which the establishment in 1971 greatly promotes the development of diagnostic methods. The traditional ELISA is performed in a "sandwich-like" manner, in which two antibodies bind to the same antigen. Specifically, the capture antibody binds to the antigen in a sample to form a capture antibody-antigen complex, which then reacts with a detection antibody carrying a coupled enzyme capable of binding to the antigen to form a "sandwich-like" capture antibody-antigen-detection antibody complex for measurement of the activity of the coupling enzyme.

The antibody detection method has a great application value, but its detection is limited by the Kd value of the reaction between the capture antibody and the antigen. In practice, the detection limit is about 1% of the Kd value. When the concentration of an analyte is lowered to this potential detection limit, the percentage of the antibody capturing the analyte is insufficient to generate a detectable signal relative to the signal-noise ratio. Therefore, the antibody detection method using a fluorescent or chemiluminescent detection system has a detection limit of about 1 pg/mL (10-4 M for a protein having an average molecular weight of 50000 Daltons).

The intracellular interaction of a nucleic acid and a protein is commonly observed, where the nucleic acid can fold to form secondary and tertiary structures, which plays an important role in the interaction with the protein. A great progress has been made to the methods for in vitro detecting the interaction of the nucleic acid and the protein based on the diversification of the nucleotide sequences. SELEX technique is used to screen an aptamer of the selected target, and the aptamer is also called a ligand, which means that the nucleic acid can form a structure to fit the pocket of the target molecule. The screening of a target molecule ligand using the SELEX technique is performed based on the above principles.

Gold et al. (Gold L, et al. Annu Rev Biochemn, 64: 763-797) used SELEX to screen RNA and ssDNA ligands of a specific antibody of systemic lupus erythematosus in 1995, which makes a great contribution not only to the diagnosis of systemic lupus erythematosus, but also to the disease monitoring and efficacy testing. In 1999, Gold et al. (Gold L, et al. Diagn Dec.; 4(4):381-8) further investigated the resolution of a ligand microarray in the research about the application of ligand microarrays in molecular diagnosis, which indicated that the aptamer detection has great application prospects. In the prior art, the ligand is generally detected directly by PCR amplification. However, this method has the following defects, such as complicated operation, requirement of separating the ligand from the aptamer, low sensitivity (after the separation of the ligand from the aptamer, the purity of the ligand and the recombination of the residual aptamers and the ligands affect the DNA replication) and poor accuracy.

Based on the SELEX technique, aptamers respectively corresponding to various targets have been screened. In particular, many known proteins capable of binding to nucleic acids, such as T4 DNA polymerase, R17 phage envelope protein, Escherichia coli rho Factor, Escherichia coli ribosomal protein S1, phenylalanine-tRNA synthetase, autoimmune antibody capable of recognizing RNA, E2F transcription factor and various HIV-associated proteins, can act as suitable targets for SELEX technique.

The fact that SELEX technology can be used to screen ligands of various proteins has promoted the application of ligands, for example, the ligands can be used as replacements of monoclonal and polyclonal antibodies for diagnosis and treatment, which demonstrates the value of the ligands. Ligands of DNA polymerase have been used in hot-start PCR to diagnose the low-copy replicons, improving the sensitivity and fidelity of PCR. Ligands have also been used to facilitate the development of experimental methods. After subjected to fluorescence labeling, the ligand of the neutral elastase can be used in the flow cytometry of the concentration of the elastase. The ligand of the neutral elastase has also been used in the in vivo diagnosis of mouse pneumonitis model.

In the enzyme-linked oligonucleotide method (ELDNA), one or more antibodies are replaced by a ligand having high specificity and affinity to the antigen, which can be obtained by in vitro screening using the SELEX technology. U.S. Patent Nos. WO 96/40991 and WD 97/38134 both disclose the ELDNA, where an aptamer is used to replace the detection antibody or capture antibody in the "sandwich" assay. The "sandwich" assay generally uses a conventional enzyme-linked detection antibody to detect a capture molecule-antigen complex, whereas the labeling of the oligonucleotide with a reporter enzyme molecule requires a chemical synthesis process and additional labor, and there are also difficulties in the use of an antibody reagent in the above method.

The above two patents also mention the use of the PCR amplification system for the detection of an aptamer in a capture molecule-target molecule-detection molecule complex, where a PCR primer of a common reporter molecule such as enzyme and biotin is used to amplify the amplicon to increase the number of ligands. However, this method has the following disadvantages, for example, for the detection of both of the DNA and RNA ligands, there is a need to further separate the amplified ligand from the impure nucleotide primer dimer and the conventional gel separation requires a lot of manual labor. In addition, the use of labeled primers still fails to solve the problems of impureness and amplification of the primer dimer, therefore, the accurate quantification cannot be achieved. Though a significant progress has been made, the diagnostic methods still require to be improved with respect to sensitivity, manual operation and the dynamic monitoring to rapidly determine whether there is a target in a sample and quantify the target.

MALDI-TOF MS, as a novel soft ionization organic mass spectrometry, undergoes a rapid development in recent years, which has become a powerful tool for the detection and identification of polypeptides, proteins, polysaccharides, nucleotides, glycoproteins, high polymers and various synthetic polymers. The operating principle of this instrument is described as follows. When a certain intensity of laser is used to irradiate a co-crystallized film formed by the sample and the substrate, the substrate absorbs energy from the laser so that the charge transfer occurs between the substrate and the sample to ionize the sample molecules. The ionized sample molecules are accelerated by the electric field to pass through the flight tube and then respectively detected according to the time of flight to the detector, that is, the ion determination is performed based on that the mass-to-charge ratio is positively proportional to the time of flight of the ions to be detected. The core of MALDI-TOF-MS is to perform the detection based on the mass-to-charge ratio (m/z) of the sample and measure the molecular weight of the sample molecule.

It can be concluded from the operating principle that MALDI-TOF MS has the characteristics of high sensitivity, high accuracy, high resolution, simple and clear spectrum, wide mass range and rapid detection. In addition, this instrument involves easy preparation of samples, less consumption of samples and large scale, parallelization high-automation treatments of samples. This method also has special advantages in the determination of biomacromolecules and synthetic polymer. Therefore, MALDI-TOF MS has been regarded as a powerful tool for detecting and identifying polypeptides, proteins, polysaccharides, nucleotides, glycoproteins, high polymers and various synthetic polymers in recent years. For example, the MALDI-TOF MS can been applied to determine the peptide mass fingerprint (PMF) and post-source decay (PSD) fragment ion spectrum of the protein enzymatic hydrolysates to obtain sequences of the polypeptides and proteins through the combination with the search on the mass spectrometry network database. Moreover, when applied in the analysis and detection of genomic single nucleotide polymorphisms (SNPs), the MALDI-TOF MS is capable of distinguishing and identifying the DNAs having a relative molecular weight of about 7,000 (including 20-30 bases) and differing only in one base. It should be particularly noted that MALDI-TOF MS has become one of the key technologies essential for research of proteomics in the life sciences.

With the rapid development of science and technology, especially the advancement of big data processing technology, the deep understanding and application of the functional mechanism of human molecules can be promoted as long as there is sufficient data information.

SUMMARY OF THE INVENTION

The detection of serum tumor markers can be used as a non-invasive diagnostic method to play an important role in the tumor diagnosis. Therefore, it is vital for early diagnosis and prevention of tumors to establish a simple, rapid, sensitive and dynamic method for diagnosing serum tumor marker. An object of the invention is to provide technical solutions that an aptamer group can be used to capture a marker group in a detection solution, and then the resulting complex is isolated to obtain the marker group, which is subjected to qualification, quantification and omic analysis based on MALDI-TOF MS and bioinformatics tools. Therefore, this application is suitable for the detection of a composite sample such as serum and body fluids.

In a first aspect, this application provides a method for simultaneous detection of multi target molecules using a magnetic bead-aptamer complex, which is suitable for the detection and analysis of multiple markers. Specifically, the method comprises the following steps:

(1) incubation incubating the magnetic bead-aptamer complex with a target molecule-containing sample to form a magnetic bead-aptamer-target molecule complex;

(2) acid elution adding an elution buffer to the magnetic bead-aptamer-target molecule complex under shaking to collect an eluate to which Tris-HCl containing a standard peptide is added to neutralize the eluate for detection of the target molecules;

(3) subjecting the neutralized eluate to mass spectrometry for qualitative and quantitative detection of the target molecules; and (4) analyzing data from the mass spectrometry on a data analytics platform to obtain the detection results.

In an embodiment, in step (1), the target molecule-containing sample comprises at least one of serum, urine, body fluid and cell and tissue suspensions.

In an embodiment, in step (1), the aptamer is an aptamer group, screened by SELEX, specific to the target molecule-containing sample.

In an embodiment, in step (2), an efficiency of the acid elution for separating the target molecules from the aptamer is 98% or more.

In an embodiment, in step (2), the standard peptide is a reference standard peptide that is introduced in a mass spectrometric sample for accurate qualification and quantification of a specified peptide.

In an embodiment, in step (3), the target molecules which are obtained by screening have a specific marker.

In an embodiment, in step (4), a functional mechanism of a specified protein is speculated based on a dose-effect relationship, and an analysis report is made.

In an embodiment, in step (1), the target-containing sample is prepared by the following steps:

collecting the required amount of blood by venipuncture; immediately removing a needle and injecting the blood into a test tube containing an anticoagulant; immediately shaking the test tube gently to mix the blood and the anticoagulant uniformly to avoid coagulation; and centrifuging the test tube at 3,000-6,000 rpm to obtain a serum sample.

In an embodiment, in step (1), the magnetic bead-aptamer-target molecule complex is prepared by the following steps: incubating 100 µL of the target-containing sample with 50 µL of the magnetic bead-aptamer complex at 37° C. for 30 min, washing the reaction mixture once with 3×SSC; and washing the reaction mixture three times with 0.4 mM binding buffer each for a volume of 20 times the volume of the reaction mixture followed by magnetic separation to obtain the magnetic bead-aptamer-target molecule complex.

In an embodiment, in step (2), the acid elution comprises the steps of: adding 0.5 mL of the elution buffer to the magnetic bead-aptamer-target molecule complex obtained in step (1) followed by shaking for 1 min to collect the eluate; and immediately neutralizing the eluate with 250 µL of 1 M Tris-HCl (pH 8.0); repeating the elution and neutralization twice; and combining the neutralized eluates to obtain a target molecule solution for mass spectrometry.

In a second aspect, this application provides a kit for simultaneous detection of multi target molecules using a magnetic bead-aptamer complex, which comprises:

5-10 mL of an A reagent, comprising 0.01-0.1 M phosphate buffer at pH 7.4 containing 50% of streptavidin agar magnetic beads with a particle size of 5-50 nm;

5-10 mL of a B reagent, comprising 0.4 mM 1× binding buffer at pH 7.4 containing 0.003-0.3 µg/L of a specific biotinylated aptamer; and a C reagent which is an elution buffer.

In an embodiment, the elution buffer comprises glycine, sodium chloride and Tween 20.

In a third aspect, this application provides a system for simultaneous detection and analysis of multiple molecules, comprising:

at least one first reagent comprising a magnetic bead carrier having a specific aptamer group on the surface;

at least one second reagent comprising an eluent;

at least one detection instrument comprising a mass spectrometer; and at least one data platform comprising a data-analysis instrument and corresponding software;

wherein the specific aptamer group is an aptamer group specific to a specific molecule in a composite sample; and the magnetic bead carrier is prepared by coating the specific aptamer group onto magnetic beads and is capable of specifically binding markers; the detection instrument is used to determine a content of the specific molecule in a neutralized eluate by laser desorption TOF mass spectrometry after combined magnetic beads are eluted; and the data-analysis instrument is used to analyze the dose-effect relationship of the specific target molecule detected by mass spectrometry to determine molecular interrelationship and functional correlation.

In an embodiment, the specific aptamer group is screened by SELEX.

In an embodiment, the mass spectrometer is used for qualitative and quantitative detection of multi target molecules bound to the specific aptamer group.

In an embodiment, the data analysis instrument is used to analyze and determine the probability of occurrence and the reference result of the pathogenesis according to the functional mechanism of a pathogenic molecule and the nature and content of a specific marker in the diagnosis of a disease.

The method, which is capable of simultaneously detecting multiple markers and providing the analysis result, has the following beneficial effects.

The magnetic beads are used herein as carriers to bind a target molecule (non-nucleic acid molecule) through the specific aptamer to form a complex, which is then qualitatively and quantitatively analyzed by mass spectrometry, and the obtained data are summarized and analyzed to obtain omic-analysis results, so that this method can be used for the detection and/or bioinformatics analysis of signals of non-nucleic acid ligands. Moreover, this method involves the rapid, highly-sensitive, highly-specific and complete multi-ligand microarray detection, inductive analysis and simple and mechanical operation. Magnetic beads (such as agar magnetic beads), as carriers, can be used to bind a target molecule to form a complex, which is subjected to a series of processes including magnetic separation, mechanical loading, separation, elution, incubation and mass spectrometric qualification and quantification to obtain the characteristic spectrum of the target molecule. The characteristic spectrum is analyzed and processed using the data platform to give corresponding results.

Agar magnetic beads not only have low cost and good biocompatibility, but also can maintain the spatial structure of the bound molecules. The agar magnetic beads are prepared as follows: paramagnetic magnets (ferroferric oxide) are coated with agar, sealed with skim milk powder, and added with reactive groups such as carboxyl groups, epoxy groups and amino groups to obtain the agar magnetic beads having excellent ability to bind biomolecules.

The specific aptamer of the invention is screened by SELEX technique according to the specific sample. This aptamer is capable of binding a specific molecule in a sample, where the molecule is formed due to the abnormal function of an organism from which the sample is collected. Therefore, the abnormal function (i.e., the pathogenesis) occurring in the organism can be indirectly determined through the qualification and quantification of the specific molecule.

A strongly-ionic acid eluent (pH 3.0) containing 0.1 M glycine, 0.5 M sodium chloride and 0.05% Tween 20 is used in the elution to elute the molecule-binding magnetic beads under shaking for 1 min based on the magnetic binding, and the eluate is collected and immediately neutralized with 250 µL of 1 M Tris-HCl (pH 8.0). Such elution and neutralization are repeated three times and the resulting neutralized eluates are combined for mass spectrometry. In addition, the Tris-HCl buffer is introduced with a standard sample having specific peptides for qualification and quantification of the specific protein.

The specific protein is qualified and quantified using a mass spectrometer and standard peptides, and the obtained results are processed and analyzed using a data analysis platform to give reference results. In the use of the data analysis platform, the specific molecule captured by a specific aptamer obtained by SELEX screening is investigated to obtain the pathogenic mechanism of a disease, and a specific marker protein group involved in the mechanism is analyzed with respect to the protein property and amount to determine the pathogenic and/or physiological mechanism. The data analysis platform is established according to the relationship between the pathogenic and/or physiological mechanism and the nature and quantity of respective molecules determined by mass spectrometry.

The entire detection process, including automatic sample loading, incubation, elution, relative qualification and quantification by mass spectrometry, data analysis using data platform and report generation, can be mechanically completed by the detection instruments. In addition, the processes of sample loading, reagent adding, elution, mass spectrometry, multi-molecular data processing and result analysis all can be mechanically performed, enabling high mechanization degree. A large amount of information can be generated through the multi-molecule detection to comprehensively reflect the overall condition of the organism and the basic function mechanism. The specific aptamer of the invention is screened by SELEX technique according to the specific sample. This aptamer is capable of binding a specific molecule in a sample, where the molecule is formed due to the abnormal function of an organism from which the sample is collected. Therefore, the abnormal function (i.e., the pathogenesis) occurring in the organism can be indirectly determined through the qualification and quantification of the specific molecule. Mass spectrometry is a desirable tool for multi-molecule detection, specifically, it can not only systematically detect the specific target molecules captured by the aptamer in a sample, but also excellently reflect the dose-effect relationship among the molecules, facilitating the comprehensive understanding of the organism function.

The invention uses the specific binding between the aptamer and the ligand to enhance the specificity of the detection, so that it has high sensitivity and strong specificity. The mass spectrometry is coupled with an accurate information collection and processing system to process the large amount of collected data. Moreover, a reliable data report can be exported since the information acquisition and processing of the invention is completed by mass spectrometry.

The detection involves the use of a single vessel and simple operation, and the data acquisition and processing can be completed under a completely-closed condition, effectively ensuring the safety and cleanness of the detection. The operation is simple and convenient since it is only required to co-incubate the aptamer and the ligand at room temperature for 45 min to complete the binding, facilitating the wide application in a general laboratory or clinical department. Additionally, in this application, the assembled kit or the constructed biochip can be widely used in basic research and clinical testing, bringing certain economic and social benefits.

In summary, for the kit using the magnetic bead-aptamer-multi-molecule mass spectrometry of the invention to simultaneously detect a protein (such as a non-nucleic acid target molecule) and a gene, an aptamer beacon molecule (the molecule has been applied for a patent CN1521272 titled "Novel Ligand Detection Method") is used to bind a protein ligand through the aptamer to form a ligand-aptamer beacon molecule complex, so that the ligand information of the target molecule is converted into nucleic acid beacon information to associate the target molecule information with the nucleic acid gene information. Then the target molecule and the nucleic acid gene are simultaneously detected by real-time quantitative PCR. The kit of the invention adopts a specific aptamer group and magnetic separation to extract and separate target molecules, and the difference from the prior art is that mass spectrometry is used to collect information of multiple target molecules in a composite sample, so that the qualification and quantification of multi target molecules is achieved, providing overall data information to better understand biological functions. The kit not only has simple operation and low cost, but also has the characteristics of rapid detection, high sensitivity, strong specificity, large molecular information content and mechanization, playing a significant role in research on the genomics and proteomics of pathogens.

BRIEF DESCRIPTION OF THE DRAWINGS

The present invention will be further described in detail below with reference to the accompanying drawings and embodiments.

DETAILED DESCRIPTION OF EMBODIMENTS

Figure 1:
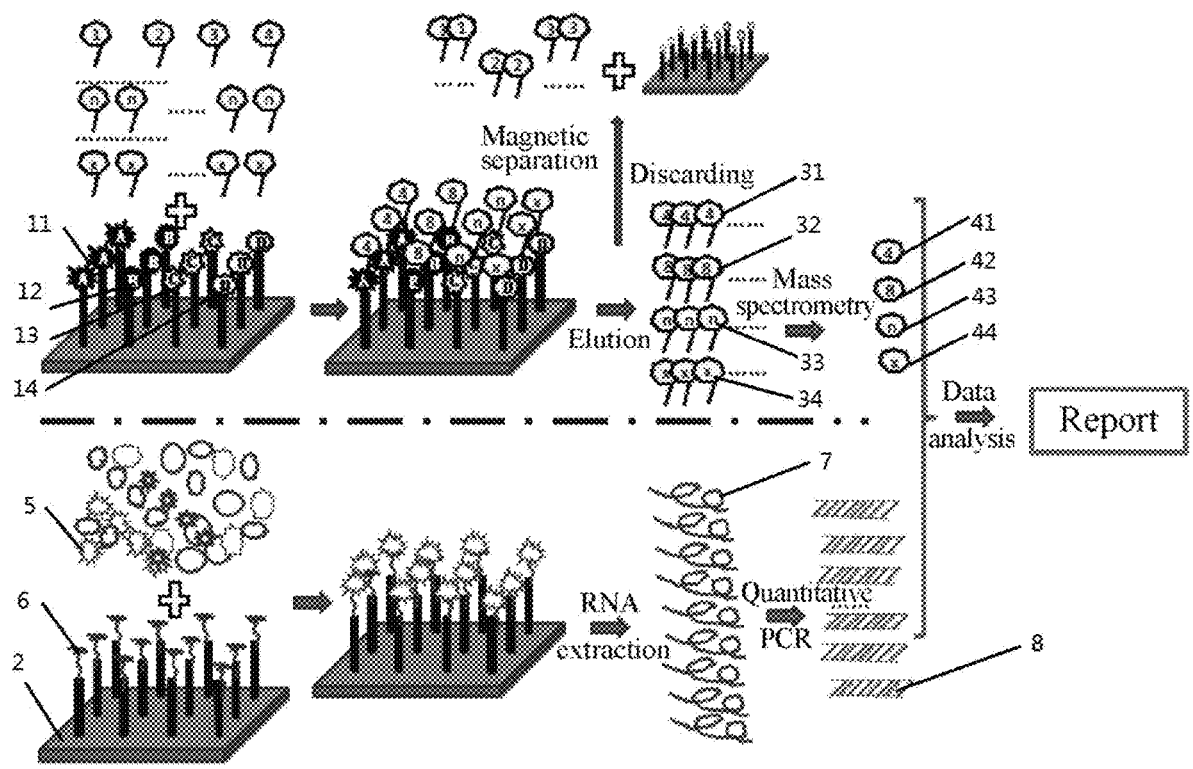
FIG. 1 schematically shows Embodiment 1 of the invention. It should be noted that in FIG. 1, aptamers A, B, C and D are aptamers of p120 and p24 antigens. CD4 and membrance protein antibody and antigen.

In Figures:

11 Aptamter A; 12 Aptamter B; 13 Aptamter C; 14 Aptamter D;

2 Magnetic bead carrier;

31 Protein ligand of aptamer A; 32 Protein ligand of aptamer B; 33 Protein ligand of aptamer C; 34 Protein ligand of aptamer D;

41 Maker peptide of protein ligand 4; 42 Maker peptide of protein ligand 8; 43 Maker peptide of protein ligand n; 44 Maker peptide of protein ligand x;

5 HIV virus;

6 Aptamer of HIV virus;

7 Viral RNA;

8 PCR product.

(1) A sample to be detected is degreased, specifically, the sample is cooled to 4° C. and centrifuged at 3,000 rpm for 20 min, and the upper lipid layer is discarded.

(2) The degreased sample is added to a 0.4 mM binding buffer containing magnetic beads carrying a specific aptamer group to allow a target molecule to bind to the magnetic beads.

(3) The target molecule-binding magnetic beads are washed once with 3×SSC buffer (pH 7.4), and then washed three times with the binding buffer each for a volume of 10 times the volume of the magnetic beads.

(4) The specific marker-binding magnetic beads are eluted with a basic buffer, and the resulting eluate is neutralized with an acidic buffer in a volume ratio of 2:1 to form a target molecule extract.

(The above steps (2)-(4) can be performed in one time by a magnetic bead washing-extracting machine or the like).

(5) The target molecule extract is analyzed by laser-resolution TOF mass spectrometry to determine the content of a specific protein in the sample.

(6) The obtained specific protein content is analyzed and processed by a data platform to determine the pathogenesis of a disease and recommend a treatment regimen.

In an embodiment, a kit of this application includes 5-10 mL of a reagent 1, 5-10 mL of a reagent 2 and a reagent 3, where the reagent 1 is a 0.01-0.1 M pH 7.4 phosphate buffer containing 50% of streptavidin agar magnetic beads with a particle size of 5-50 nm; the reagent 2 is a 0.4 mM pH 7.4 1× binding buffer containing 0.003-0.3 μg/L of a specific biotinylated aptamer; and the reagent 3 is an elution buffer.

Specifically, the agar magnetic beads are bound with the streptavidin via a carboxyl group (or an epoxy group), and then bound with a biotinylated aptamer to form a carrier for the target molecule binding (containing 0.01% sodium azide as a preservative).

0.4 mM pH 7.4 binding buffer containing 0.01% sodium azide as a preservative is used for the binding between the aptamer and the target molecule, where 1 L 1× binding buffer is prepared as follows. A solution containing 138 mmol/L NaCl, 2.7 mmol/L KCl, 8.1 mmol/L Na2HPO4, 1.1 mmol/L KH2PO4 and 1 mmol/L MgCl2 is first prepared, adjusted to pH 7.4 with HCl, dilute to 1 L with water, sterilized by high pressure steam for 20 min and stored at room temperature for use.

The target molecule-binding magnetic beads are washed with 3×SSC buffer (pH 7.4).

The target molecule-binding magnetic beads are eluted with a pH 3.0 basic eluent (containing 0.1 M glycine, 0.5 M sodium chloride and 0.05% Tween 20) in a volume ratio of 1:2 under shaking for 1 min, and the eluate is collected.

The eluate is neutralized with a pH 8.0 acidic buffer (250 μL of 1 M Tris-HCl) containing a standard peptide reagent in a volume ratio of 2:1.

In an embodiment, this application provides a method for simultaneous detection of multi target molecules using a magnetic bead-aptamer complex, where magnetic beads coated with a specific aptamer are used to extract the target molecule group, and then the target molecule group is subjected to qualification and quantification by MS, finally, the obtained results are analyzed by a data platform to give the reference results. The method specifically includes the following steps.

(1) Sample preparation

The required amount of blood is collected by venipuncture, and the needle is immediately removed. The blood is injected into a test tube containing an anticoagulant, and immediately shaken gently to mix the blood and the anticoagulant uniformly to avoid coagulation. Then, the test tube is centrifuged at 3,000-6,000 rpm to obtain a serum sample.

(2) Formation of a magnetic bead-aptamer-target molecule complex

100 μL of the serum sample is incubated with 50 μL of a magnetic bead-aptamer complex at 37° C. for 30 min. The reaction mixture is washed once with 3×SSC, and then washed three times with 0.4 mM binding buffer each for a volume of 20 times the volume of the reaction mixture. The reaction mixture is magnetically separated to obtain the magnetic bead-aptamer-target molecule complex.

(3) Preparation of a target molecule sample

The magnetic bead-aptamer-target molecule complex is added with 0.5 mL of a pH 3.0 elution buffer containing 0.1 M glycine, 0.5 M sodium chloride and 0.05% Tween 20 and shaken for 1 min. The eluate is collected and immediately neutralized with 250 μL of 1 M Tris-HCl (pH 8.0) containing a standard peptide for qualification and quantification. Such elution and neutralization are repeated three times and the resulting three eluates are combined to produce a target molecule solution for mass spectrometry.

(4) Mass spectrometry

The target molecule solution is qualitatively and quantitatively determined by mass spectrometry to obtain the information about the target molecule.

(5) The obtained data are analyzed by data platform and an analysis report is generated.

The invention is further described below with reference to embodiments.

Example 1 Shortening of Window Period by Simultaneous Detection of Multiple Proteins and Genes Referring to FIG. 1, the proteins and genes were both qualitatively and quantitatively analyzed to determine the status of HIV infection, such as window period, silent period and outbreak period.

Sample Preparation (Serum)

After the required materials were prepared, labeled and checked, the required amount of blood was collected by venipuncture, and the needle was immediately removed. The blood was injected into a test tube containing an anticoagulant, and the test tube was immediately shaken gently to mix the blood and the anticoagulant uniformly to avoid coagulation. Then the test tube was centrifuged at 3,000-6,000 rpm to obtain a serum sample which was stored at 4° C. for use.

Preparation of aptamers respectively of P24 antigen, P24 antibody, CD4 and viral envelope antibody The specific aptamers respectively of P24 antigen, P24 antibody, CD4 and virus envelope antibody were obtained by SELEX.

Preparation of magnetic bead-aptamer-multi-protein (including P24 antigen, P24 antibody, CD4 and virus envelope antibody) "sandwich" complex Streptavidin magnetic beads were selected, added with biotinylated aptamers (including aptamers of P24 antigen, P24 antibody, CD4 and virus envelope antibody) and incubated for 30 min to produce a magnetic bead-aptamer complex. The magnetic bead-aptamer complex is washed 3 times with PBS containing 0.05% Tween 20 each for 3 min. 10-100 μL of the above magnetic bead-aptamer complex was added to 100-1000 μL of the serum sample. The reaction mixture was incubated for 30 min for binding to form a magnetic bead-aptamer-multi-protein complex. The magnetic bead-aptamer-multi-protein complex was adhered by an electromagnetic pole to be isolated from the unbound serum. After the serum was aspirated, the magnetic bead-aptamer-multi-protein complex was washed 3-12 times with 0.01-0.1 M PBS containing 0.01-0.1 M Tween 20 each for 400 μL and 3-6 min.

Preparation of a Solution for Mass Spectrometry

The acid elution was performed as follows. The magnetic bead-aptamer-multi-protein complex was eluted with 0.5 mL of an elution buffer (pH 3.0) containing 0.1 M glycine, 0.5 M sodium chloride and 0.05% Tween 20 under shaking for 1 min. The resulting eluate was collected and immediately neutralized with 250 μL of 1 M Tris-HCl (pH 8.0). Such elution and neutralization were repeated three times, and the resulting three eluates were collected and combined.

MS Detection

The multiple proteins including P24 antigen, P24 antibody, CD4 and virus envelope antibody were qualitatively and quantitatively determined by a mass spectrometer.

Gene Detection

The serum was added to nucleic acid-extracting magnetic beads to produce a nucleic acid-magnetic bead complex. The nucleic acid-magnetic bead complex was lysed by a lysis buffer, washed and eluted, and the eluate was subjected to reverse transcription-PCR amplification.

The data was collected, processed and analyzed.

A detection report was generated and printed.

This method can simultaneously detect and analyze RNA, p120 and p24 antigens, CD4 and a membrane protein antibody and antigen, which facilitates the comprehensive understanding of the patient's condition, providing a reasonable therapeutic regimen.

Example 2 Detection of Multiple Tumor Makers

Figure 2:
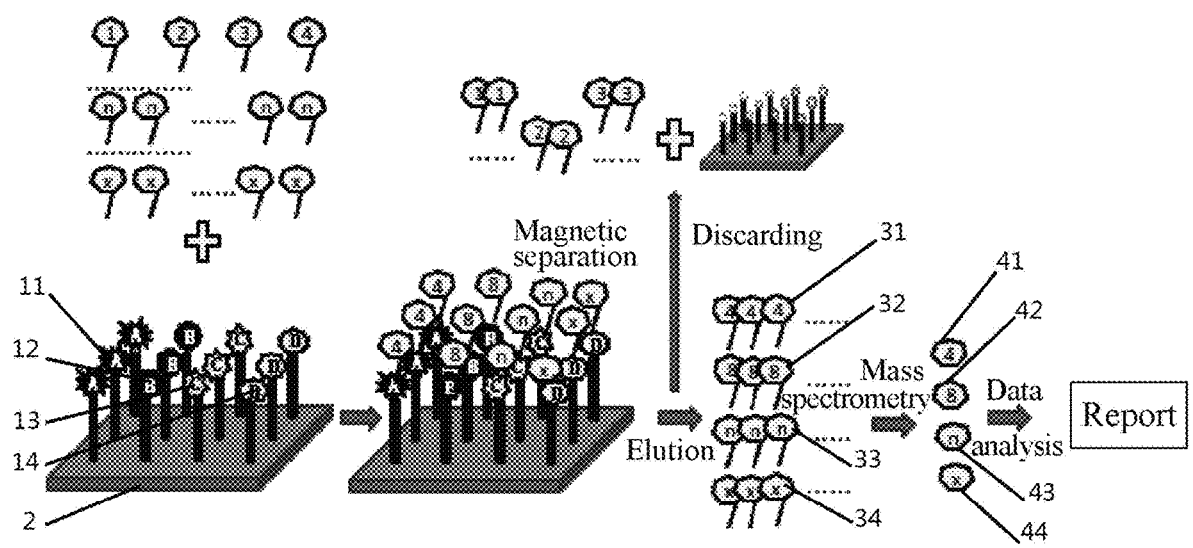
FIG. 2 schematically shows Embodiment 2 of the invention; It should be noted that in FIG. 2, aptamer A is a specific aptamer shared by gastric cancer, liver cancer and lung cancer; aptamer B is a specific aptamer of gastric cancer; aptamer C is a specific aptamer of liver cancer; and D is a specific aptamer of lung cancer.

Referring to FIG. 2, the occurrence of a tumor and the type of a cancer (gastric cancer, lung cancer and liver cancer) were determined by the dose-effect relationship of the corresponding peptides.

Preparation of a Serum Sample

After the required materials were prepared, labeled and checked, the required amount of blood was collected by venipuncture, and the needle was immediately removed. The blood was injected into a test tube containing an anticoagulant, and the test tube was immediately shaken gently to mix the blood and the anticoagulant uniformly to avoid coagulation. Then the test tube was centrifuged at 3,000 rpm to obtain a serum sample which was stored at 4° C. for use.

Preparation of a Tumor Marker Aptamer

Gastric cancer, liver cancer and lung cancer serums were respectively used as a composite target molecule (non-gastric cancer serum as control) to obtain their corresponding aptamers by SELEX, where the apatmer which was shared by the three tumors was used as a tumor marker aptamer.

Preparation of a Magnetic Bead-Tumor Marker Aptamer Complex

Streptavidin magnetic beads were added with a biotinylated tumor marker aptamer and incubated for 30 min to produce a magnetic bead-aptamer complex. The magnetic bead-aptamer complex was washed 3 times with PBS containing 0.05% Tween 20 each for 3 min.

Preparation of a Magnetic Bead-Aptamer-Multi Tumor Marker "Sandwich" Complex 10-100 μL of the above agar magnetic bead-tumor marker aptamer complex was added to 100-1000 μL of the serum sample. The reaction mixture was incubated for 30 min for binding to produce a magnetic bead-aptamer-multi-protein complex. The magnetic bead-aptamer-multi-protein complex was adhered by an electromagnetic pole to be isolated from the unbound serum. After the serum was aspirated, the magnetic bead-aptamer-multi-protein complex was washed 3-12 times with 0.01-0.1 M PBS containing 0.01-0.1 M Tween 20 each for 400 μL and 3-6 min.

Preparation of Multiple Tumor Markers

The acid elution was performed as follows. The magnetic bead-aptamer-multi-tumor marker complex was eluted with 0.5 mL of an elution buffer (pH 3.0) containing 0.1 M glycine, 0.5 M sodium chloride and 0.05% Tween 20 under shaking for 1 min. The resulting eluate was collected and immediately neutralized with 250 μL of 1 M Tris-HCl (pH 8.0) containing a standard peptide for the detection of a target molecule. Such elution and neutralization were repeated three times, and the resulting three eluates were combined to give a mixture of multiple tumor markers.

MS Detection

The multiple target molecules were qualitatively and quantitatively determined using a mass spectrometer according to the standard peptide in the mixture. The data was collected, processed and analyzed. In the case that the marker molecules extracted by the three types of tumor aptamers were identified by mass spectrometry to be a common marker molecule, it was confirmed that a tumor occurred. The specific marker molecules respectively corresponding to the three types of tumors can be used for the identification of a tumor.

A test report was generated and printed.

Figure 3:
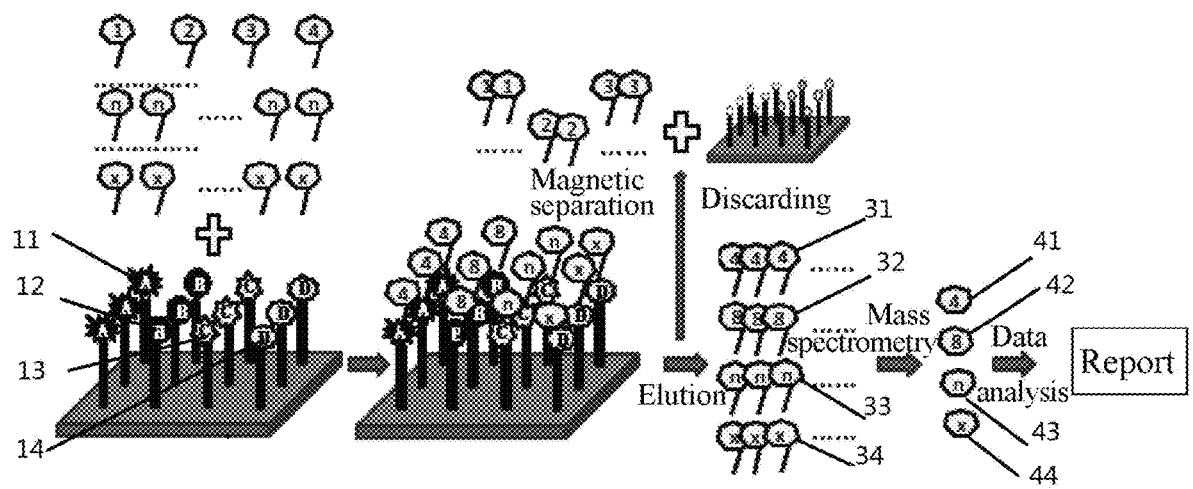
FIG. 3 schematically shows Embodiment 3 of the invention. It should be noted that in FIG. 3, aptamer A is a specific aptamer of gastric cancer trauma; aptamer B is a specific aptamer of induced gastric cancer stem cells; aptamer C is a specific aptamer of autophagic antibody of gastric cancer; and D is a specific aptamer of gastric cancer.

Example 3 Detection of Multiple Marker Molecules Associated with Gastric Cancer Pathogenesis Referring to FIG. 3, the pathogenesis of gastric cancer was determined according to the dose-effect relationship of a peptide.

Preparation of a Serum Sample

After the required materials were prepared, labeled and checked, the required amount of blood was collected by venipuncture, and the needle was immediately removed. The blood was injected into a test tube containing an anticoagulant, and the test tube was immediately shaken gently to mix the blood and the anticoagulant uniformly to avoid coagulation. Then the test tube was centrifuged at 3,000-6,000 rpm to obtain a serum sample which was stored at 4° C. for use.

Preparation of an Aptamer of Multiple Marker Molecules Associated with the Pathogenesis of Gastric Cancer Gastric cancer serum (non-gastric cancer serum as control) was used as a composite target molecule to obtain a gastric cancer marker aptamer by SELEX.

Preparation of a Magnetic Bead-Gastric Cancer Marker Aptamer Complex

Streptavidin magnetic beads were added with a biotinylated gastric cancer marker aptamer. The reaction mixture was incubated for 30 min to form a magnetic bead-aptamer complex. Then the magnetic bead-aptamer complex was washed 3 times with PBS containing 0.05% Tween 20 each for 3 min.

Preparation of a Magnetic Bead-Aptamer-Gastric Cancer Marker "Sandwich" Complex 10-100 μL of the above agar magnetic bead-gastric cancer marker aptamer complex was added to 100-1000 μL of the serum sample and incubated for 30 min for binding to produce a magnetic bead-aptamer-gastric cancer marker complex. The magnetic bead-aptamer-gastric cancer marker complex was adhered by an electromagnetic pole to be isolated from the unbound serum. After the serum was aspirated, the magnetic bead-aptamer-gastric cancer marker complex was washed 3-12 times with 0.01-0.1 M PBS containing 0.01-0.1 M Tween 20 each for 400 μL and 3-6 min.

Preparation of Multiple Gastric Cancer Markers

The acid elution was performed as follows. The magnetic bead-aptamer-gastric cancer marker complex was eluted with 0.5 mL of an elution buffer (pH 3.0) containing 0.1 M glycine, 0.5 M sodium chloride and 0.05% Tween 20 under shaking for 1 min. The resulting eluate was collected and immediately neutralized with 250 μL of 1 M Tris-HCl (pH 8.0) containing a standard peptide for the detection of the target molecule. Such elution and neutralization were repeated three times, and the resulting three eluates were collected and combined to give a mixture of multiple tumor markers.

MS Detection

The multiple target molecules were qualitatively and quantitatively determined using a mass spectrometer according to the standard peptide in the mixture.

Data Collection, Processing and Analysis

The marker target molecules associated with the pathogenesis of gastric cancer were extracted by the gastric tumor aptamers and identified by mass spectrometry to summarize the pathogenesis of gastric cancer.

A test report was generated and printed.

INDUSTRIAL APPLICABILITY

The invention relates to molecular biology, and more specifically to a method and a kit for simultaneous detection of multi target molecules using a magnetic bead-aptamer complex. The method includes the steps of screening out a specific aptamer; quantitatively and qualitatively detecting a target molecule group by mass spectrometry; and processing data and providing an analysis report by a data platform, which enables the simultaneous detection of related multiple target molecules. In addition, the condition of the entirety or a certain function can be comprehensively and clearly shown based on the data analysis of multiple target molecules. The invention uses a specific aptamer to capture the related target molecule group, and then the target molecules were qualitatively and quantitatively analyzed by mass spectrometry to relatively comprehensively reflect the change in function of the body or tissue. Moreover, this method can provide a large amount of data, which greatly improves the accuracy of the omic analysis. Therefore, the invention is of great significance for proteomics and genomics research and clinical molecular detection.

It should be understood that various modifications and changes made by those skilled in the art based on the above description should fall within the scope defined by the appended claims.

These embodiments are merely illustrative of the invention, and are not intended to limit the invention. The modifications made without departing from the spirit of the invention, or the direct use of the technical solutions of the invention in other occasions, should fall within the scope of the invention.

What is claimed is:

1. A method for simultaneous detection of multi target molecules using a magnetic bead-aptamer complex, comprising:

(1) incubation incubating the magnetic bead-aptamer complex with a target molecule-containing sample to form a magnetic bead-aptamer-target molecule complex, wherein the aptamer are a group of aptamers screened by SELEX and specific to the target molecule-containing sample; and further comprising the step of:

preparing the magnetic bead-aptamer-target molecule complex by incubating 100 µL of the target molecule-containing sample with 50 µL of the magnetic bead-aptamer complex at 37° C. for 30 min, washing the reaction mixture once with 3×SSC; and washing the reaction mixture three times with 0.4 mM binding buffer each for a volume of 20 times the volume of the reaction mixture followed by magnetic separation to obtain the magnetic bead-aptamer-target molecule complex:

(2) acid elution adding an elution buffer to the magnetic bead-aptamer-target molecule complex under shaking to collect an eluate to which Tris-HCl containing a standard peptide is added to neutralize the eluate for detection of the target molecules, wherein the acid elution comprises the steps of:

adding 0.5 mL of the elution buffer to the magnetic bead-aptamer-target molecule complex obtained in step (1) followed by shaking for 1 min to collect the eluate; and immediately neutralizing the eluate with 250 µL of 1 M Tris-HCl (pH 8.0): repeating the elution and neutralization twice; and combining the neutralized eluates to obtain a target molecule solution for mass spectrometry;

(3) subjecting the neutralized eluate to mass spectrometry for qualitative and quantitative detection of the target molecules; and (4) analyzing data from the mass spectrometry on a data analytics platform to obtain the detection results.

2. The method according to claim 1, wherein that in the step (1), the target molecule-containing sample comprises at least one of serum, urine, body fluid and cell and tissue suspensions.

3. The method according to claim 1, wherein that in the step (2), an efficiency of the acid elution for separating the target molecules from the aptamer is 98% or more.

4. The method according to claim 1, wherein that in the step (2), the standard peptide is a reference standard peptide that is introduced in a mass spectrometric sample for accurate qualification and quantification of a specified peptide.

5. The method according to claim 1, wherein that in the step (3), the target molecules which are obtained by screening have a specific marker.

6. The method according to claim 1, wherein that in the step (4), a functional mechanism of a specified protein is speculated based on a dose-effect relationship, and an analysis report is made.

7. The method according to claim 1, wherein that in the step (1), the target molecule-containing sample is prepared by the following steps:

collecting the required amount of blood by venipuncture; immediately removing a needle and injecting the blood into a test tube containing an anticoagulant;

immediately shaking the test tube gently to mix the blood and the anticoagulant uniformly to avoid coagulation; and centrifuging the test tube at 3,000-6,000 rpm to obtain a serum sample.

\* \* \* \* \*